(12) United States Patent
Ron et al.

(10) Patent No.: US 7,198,909 B1
(45) Date of Patent: Apr. 3, 2007

(54) MYELOID PRECURSOR CELL USEFUL FOR GENE THERAPY AND FOR MODULATION OF IMMUNE RESPONSES

(75) Inventors: Yacov Ron, East Brunswick, NJ (US); Joseph P. Dougherty, Hampton, NJ (US); Chiann-Chyi Chen, East Brunswick, NJ (US)

(73) Assignee: University of Medicine & Dentistry of New Jersey, New Brunswick, NJ (US)

( * ) Notice: Subject to any disclaimer, the term of this patent is extended or adjusted under 35 U.S.C. 154(b) by 0 days.

(21) Appl. No.: 09/830,176

(22) PCT Filed: Oct. 29, 1999

(86) PCT No.: PCT/US99/25477

§ 371 (c)(1),
(2), (4) Date: Apr. 23, 2001

(87) PCT Pub. No.: WO00/26393

PCT Pub. Date: May 11, 2000

Related U.S. Application Data

(60) Provisional application No. 60/106,533, filed on Oct. 31, 1998.

(51) Int. Cl.
*C12P 21/06* (2006.01)
*C12P 21/00* (2006.01)

(52) U.S. Cl. .................................. 435/69.1; 435/70.1

(58) Field of Classification Search ............. 435/320.1, 435/5, 457, 455, 456, 236; 424/192.1, 207.1
See application file for complete search history.

(56) References Cited

U.S. PATENT DOCUMENTS

| | | | | |
|---|---|---|---|---|
| 5,246,699 | A | * | 9/1993 | Debre et al. ................ 424/85.2 |
| 5,502,176 | A | * | 3/1996 | Tenen et al. ................ 536/24.1 |
| 5,652,373 | A | * | 7/1997 | Reisner ......................... 800/11 |
| 6,207,454 | B1 | * | 3/2001 | Zsebo et al. ................. 435/455 |
| 6,472,204 | B1 | * | 10/2002 | Asada et al. ............. 435/320.1 |

OTHER PUBLICATIONS

Exp. Hematol. (1994) 22:223-230 Xu et al. Correction of the enzyme deficiency in hematopoietic cells of Gaucher patients using a clinically acceptable retroviral supernatant transduction protocol.*
Bone Marrow Transplant. 1993; 11 Suppl 1;124-7. Karlsson S, Correll PH, Xu L. Gene transfer and bone marrow transplantation with special reference to Gaucher's disease.*
Exp Hematol. 1994 Aug;22(9):857-65. Freas-Lutz DL, Correll PH, Dougherty SF, Xu L, Pluznik DH, Karlsson S. Expression of human glucocerebrosidase in murine macrophages: identification of efficient retroviral vectors.*
PNAS 92:12075-12079, Migata et al.*
Blood 86(1):141-146. Xu et al.*
Bertoncello et al., "Multiparameter Analysis of Transplantable Hemopoietic Stem Cells. II. Stem Cells of Long-term Bone Marrow-reconstituted Recipients," Exp. Hematol., vol. 16, (1988) pp. 245-249.
Goff et al., "Isolation and Properties of Moloney Murine Leukemia Virus Mutants: Use of a Rapid Assay for Release of Virion Reverse Transcriptase," J. Virol., vol. 38, No. 1, (Apr. 1981) pp. 239-248.
Humeau et al., "Successful Reconstitution of Human Hematopoiesis in the SCID-hu Mouse by Genetically Modified, Highly Enriched Progenitors Isolated From Fetal Liver," Blood, vol. 90, No. 9, (Nov. 1, 1997) pp. 3496-3506.
National Jewish Center, "Hematopoietic stem cells," Current Opinion in Immunology, vol. 4, (1992) pp. 133-139.
Lemischka, "What We Have Learned From Retroviral Marking of Hematopoietic Stem Cells," Current Topics in Microbiology and Immunology, vol. 177, 1992, pp. 59-71.
Magli et al., "Transient nature of early haematopoietic spleen colonies," Nature, vol. 295, (Feb. 11, 1982) pp. 197-199.
Metcalf et al., Haematopoietic Cells, American Elsevier Pub. Co., New York, N.Y., 1971, pp. 550.
Morrison et al., "The Long-Term Repopulating Subset of Hematopoietic Stem Cells Is Deterministic and Isolatable by Phenotype," Immunity, vol. 1, (Nov. 1994) pp. 661-673.
Persons et al., "Retroviral-Mediated Transfer of the Green Fluorescent Protein Gene Into Murine Hematopoietic Cells Facilitates Scoring and Selection of Transduced Progenitors In Vitro and Identification of Genetically Modified Cells In Vivo," Blood, vol. 90, No. 5, (Sep. 1, 1997) pp. 1777-1786.
Spangrude et al., "Long-Term Repopulation of Irradiated Mice With Limiting Numbers of Purified Hematopoietic Stem Cells: In Vivo Expansion of Stem Cell Phenotype But Not Function," Blood, vol. 85, No. 4, (Feb. 15, 1995); pp. 1006-1016.
Suda et al., "Single-cell origin of mouse hemopoietic colonies expressing multiple lineages in variable combinations," Proc. Natl. Acad. Sci. USA, vol. 80, (Nov. 1983) pp. 6689-6693.
Till et al., "A Direct Measurement of the Radiation Sensitivity of Normal Mouse Bone Marrow Cells," Radiation Research, vol. 14, (1961) pp. 213-222.

* cited by examiner

*Primary Examiner*—Joseph Woitach
(74) *Attorney, Agent, or Firm*—Licata & Tyrrell P.C.

(57) ABSTRACT

A long-lived, myeloid-committed stem cell population is disclosed. Also disclosed are methods and compositions for targeting this population with retrovirus vectors in gene therapy protocols for correcting congenital disorders of myeloid system and for potentiating immune responses to defined tumor and viral antigens.

2 Claims, 6 Drawing Sheets

*Therapeutic Vector for Gaucher Disease*

Fcγ RIIIA

LTR - Long terminal repeat
neo - Neomycin phosphotransferase gene
CD11b - CD11b promoter
Fcγ RIIIA - Immunoglobulin γ Fc receptor promoter
hGCB - Human glucocerebrosidase gene
Ψ⁺ - Encapsidation signal Human glucocerebrosidase gene
Accession numbers from Gene Bank
J03059/J03060

US 7,198,909 B1

MYELOID PRECURSOR CELL USEFUL FOR GENE THERAPY AND FOR MODULATION OF IMMUNE RESPONSES

This application claims benefit of priority under 35 U.S.C. §371 to PCT application No. PCT/US99/25477, filed Oct. 29, 1999, which claims benefit under 35 U.S.C. §119 to U.S. Provisional Patent Application Ser. No. 60/106,533, filed on Oct. 31, 1998, whose contents are incorporated herein by reference in their entireties.

FIELD OF THE INVENTION

This invention relates to the fields of molecular biology, gene therapy and hematopoiesis. Specifically, the invention provides methods and compositions for introducing exogenous genes in myeloid-specific stem cells. Stem cells so transduced continuously replenish the mature myeloid lineage for prolonged time periods.

BACKGROUND OF THE INVENTION

Several publications are referenced in this application by numerals in parentheses in order to more fully describe the state of the art to which this invention pertains. The disclosure of each of these publications is incorporated by reference herein.

Pluripotent stem cells give rise to all red blood cells, white blood cells and platelets. Stem cells are present in the circulation as well as in the bone marrow, though in smaller numbers. Ultimately, these cells leave the bloodstream and settle and proliferate in certain tissues, such as the spleen. This colonizing ability is important in the embryonic development of hematopoietic tissues. Blood cell formation occurs first in outlying extraembryonic regions of the mesoderm, then in the liver and spleen and finally in the bone marrow, where it persists throughout adult life.

The current paradigm concerning the kinetics of hematopoiesis is that only the most primitive pluripotential bone marrow (BM) stem cells can support prolonged hematopoiesis whereas more differentiated, lineage-committed stem cells can only contribute to a particular lineage for a limited period of time. All hematopoietic lineages, including the myeloid lineage, develop from pluripotential stem cells (PSC, also called primitive stem cells) which are found in bone marrow (BM) and spleen in the adult mouse (1). The accepted definition of a PSC is that it is capable of self-renewal and that it can differentiate into all lineages of the hematopoietic system (2–4). To date, a cell surface marker unique for PCS has not been found, nor do they respond specifically to any cytokine or growth factor. PCS are rare in BM (1 in 2,000–5,000 cells) and are contained within a population of BM cells with the phenotype Thy-1.1$^{10}$Lin-Sca-1$^+$ (2,3,5–7). When this population is purified by negative selection with antibodies and complement followed by positive selection by FACS sorting, it contains all BM PSC (2,3,5–7). However, the PSC constitute only 10% (at best) of that population (6, 8). The rest of the cells in this population are a mix of various uncharacterized, more differentiated stem cells.

In the early 1960's Till and McCulloch classified BM stem cells as cells that form spleen nodules containing highly replicating hematopoietic stem cells, termed colony-forming-units-spleen (CFU-S), 8–12 days post reconstitution of irradiated recipients with adult BM cells (9). It was later realized that the observed spleen nodules contained myeloid and erythroid precursors only, and that their capacity to replenish the myeloid and erythroid lineages was transient at best. (10). More recent studies have shown that only the most primitive pluripotential BM stem cells can support hematopoiesis for long periods of time (2, 11–13). This observation is mostly based upon experiments in which the reconstitution potential of the PCS containing subpopulation (Thy-1.1$^{lo}$ LinSca-1$^+$ cells) was compared to that of the remaining BM cells. In these experiments, only the PSC-enriched population could protect a lethally-irradiated host indefinitely (2, 6, 7).

Further support for this notion came from studies on the kinetics of hematopoiesis. Studies using retroviral-mediated tagging of BM-derived PSC with a reporter gene have shown that, for a short time immediately following the reconstitution of a lethally-irradiated mouse, many stem cell clones contribute to hematopoiesis. However, a few weeks later, only very few clones were contributing to the continuous replenishment of all hematopoietic lineages (14, 15). These results suggest that for a short time after reconstitution, both lineage-committed as well as PSC contribute to hematopoiesis but the more mature, lineage-committed cells are short-lived and therefore disappear within a few weeks. Similar conclusions were reached by Harrison et al. Using a competitive repopulation assay (16), these authors showed that the appearance of all 3 hematopoietic lineages is highly correlated with respect to time which they interpreted as an indication that most donor cells arise from the same PSC and therefore, lineage-committed precursors present in the inoculum could not have contributed significantly to any of the lineages.

SUMMARY OF THE INVENTION

A long-lived myeloid committed stem cell population is disclosed in accordance with the present invention. Also provided are methods and compositions for targeting this population with retrovirus vectors in gene therapy protocols for correcting congenital disorders of the myeloid system and for potentiating immune responses to defined tumor and viral antigens.

In one aspect of the invention, a composition comprising the transduced myeloid specific stem cells in a biological carrier medium are provided. These cells are suitable for reinfusion into a test subject for the treatment of genetic disorders, such as lysosomal storage diseases. In a preferred embodiment, the transduced myeloid specific stem cells express a beneficial myeloid specific protein selected from the group consisting of glucocerebrosidase, hexosaminidase A, iduronate-2-sulphatase, sphingomyelinase and arylsulfatase A. In order to enhance expression of beneficial myeloid specific proteins, the nucleic acids encoding the same are operably linked to myeloid specific promoters within the retroviral vectors of the invention. Retroviral vectors encoding glucocerebrosidase, hexosaminidase A, iduronate-2-sulphatase, sphingomyelinase and arylsulfatase A are therefore contemplated to be within the scope of the present invention. An exemplary retroviral vector for the treatment of Gauchers disease is depicted in FIG. 8.

In a further embodiment of the invention, methods are provided for introducing heterologous nucleic acids encoding beneficial myeloid specific proteins into the myeloid specific stem cells of the invention. The method comprises obtaining myeloid-committed stem cells from a test subject and contacting the cells with a retroviral vector containing at least one nucleic acid encoding a myeloid specific protein, under conditions whereby said vector enters cells and expresses a protein encoded by said at least one nucleic acid.

In a preferred embodiment the nucleic acid is operably linked to a myeloid specific promoter. Exemplary embodiments include a method for the treatment of Tay Sachs disease, wherein the myeloid specific stem cells express hexosaminidase A; a method for the treatment of Niemann-Pick disease, wherein the myeloid specific stem cells express sphingomyelinase; a method for the treatment of Gauchers disease, wherein the myeloid specific stem cells express glucocerebrosidase; a method for the treatment of Hunter Syndrome, wherein the myeloid specific stem cells express the iduronate-2 sulphatase gene; and a method for the treatment of metachromatic leukodystrophy, wherein the myeloid specific stem cells express arylsulfatase A.

In yet another aspect of the invention, compositions and methods are provided for the potentiating immune responses to predetermined antigens of viral or tumor origin. Retroviral vectors encoding the antigens are introduced into the myeloid stem cells of the invention and the cells so transduced are then reinfused into a test subject. Exemplary tumor antigens for this purpose include, but are not limited to MAGE1 and MAGE3, tyrosinase, p21 Ras, CEA, Lewis, CD44, mut EGFR, EBNA-1, CD10, PSA, p53, BCR-able and mucin. Exemplary viral antigens for this purpose include, but are not limted to gp120 from HIV, hepatitis B virus surface antigen, herpes simplex I viral antigen, herpes simplex II viral antigen and papilloma virus antigen.

The following definitions are provided to facilitate an understanding of the present invention.

"Nucleic acid" or a "nucleic acid molecule" as used herein refers to any DNA or RNA molecule, either single or double stranded and, if single stranded, the molecule of its complementary sequence in either linear or circular form. In discussing nucleic acid molecules, a sequence or structure of a particular nucleic acid molecule may be described herein according to the normal convention of providing the sequence in the 5' to 3' direction. With reference to nucleic acids of the invention, the term "isolated nucleic acid" is sometimes used. This term, when applied to DNA, refers to a DNA molecule that is separated from sequences with which it is immediately contiguous in the naturally occurring genome of the organism in which it originated. For example, an "isolated nucleic acid" may comprise a DNA molecule inserted into a vector, such as a plasmid or virus vector, or integrated into the genomic DNA of a prokaryotic or eukaryotic cell or host organism.

When applied to RNA, the term "isolated nucleic acid" refers primarily to an RNA molecule encoded by an isolated DNA molecule as defined above. Alternatively, the term may refer to an RNA molecule that has been sufficiently separated from other nucleic acids with which it would be associated in its natural state (i.e., in cells or tissues). An isolated nucleic acid (either DNA or RNA) may further represent a molecule produced directly by biological or synthetic means and separated from other components present during its production.

A "promoter" is a DNA sequence located proximal to the start of transcription at the 5' end of an operably linked transcribed sequence. The promoter may contain one or more regulatory elements or modules which interact in modulating transcription of the operably linked gene. Myeloid cell specific promoters are provided in U.S. Pat. No. 5,502,176, the entire disclosure of which is incorporated by reference herein.

"Operably linked" describes two macromolecular elements arranged such that modulating the activity of the first element induces an effect on the second element. In this manner, modulation of the activity of a promoter element may be used to alter and/or regulate the expression of an operably-linked coding sequence. For example, the transcription of a coding sequence that is operably-linked to a promoter element is induced by factors that "activate" the promoter's activity; transcription of a coding sequence that is operably-linked to a promoter element is inhibited by factors that "repress" the promoter's activity. Thus, a promoter region is operably-linked to the coding sequence of a protein if transcription of such coding sequence activity is influenced by the activity of the promoter. The phrase "consisting essentially of" when referring to a particular nucleotide or amino acid means a sequence having the properties of a given SEQ ID No:. For example, when used in reference to an amino acid sequence, the phrase includes the sequence per se and molecular modifications that would not affect the basic and novel characteristics of the sequence.

A retroviral vector refers to a specially constructed retrovirus lacking certain essential viral protein coding regions suitable for introducing exogenous, heterologous genes into a test subject. Exemplary retroviral vectors of the invention are shown in FIGS. 1 and 8.

A "beneficial myeloid specific protein" is one which represents the wild type protein suitable for correcting a lysosomal storage disease, such as wild-type glucocerebrosidase for the treatment of Gauchers disease sphingomyelinase for the treatment of Niemann-Pick disease or hexoaminidase A for the treatment of Tay Sachs disease.

An "immune response" signifies any reaction produced by an antigen, such as a viral antigen, in a host having a functioning immune system. Immune responses may be either humoral in nature, that is, involve production of immunoglobulins or antibodies, or cellular in nature, involving various types of B and T lymphocytes, dendritic cells, macrophages, antigen presenting cells and the like, or both. Immune responses may also involve the production or elaboration of various effector molecules such as cytokines, lymphokines and the like. Immune responses may be measured both in in vitro and in various cellular or animal systems. Such immune responses may be important in protecting the host from disease and may be used prophylactically and therapeutically.

A "viral antigen" shall be any peptide, polypeptide or protein sequence, segment or epitope that is derived from a virus that has the potential to cause a functioning immune system of a host to react to said viral antigen.

An "antibody" or "antibody molecule" is any immunoglobulin, including antibodies and fragments thereof, that binds to a specific antigen. The term includes polyclonal, monoclonal, chimeric, and bispecific antibodies. As used herein, antibody or antibody molecule contemplates both an intact immunoglobulin molecule and an immunologically active portion of an immunloglobulin molecule such as those portions known in the art as Fab, Fab', F(ab')2 and F(v).

As used herein, the term "test subject" shall mean animals and human beings.

A "biological carrier medium" is any medium which is suitable for suspension and delivery of the vectors of the invention into target cells as well as a medium appropriate for reinfusion of the transduced myeloid stem cells into a test subject. Such carrier mediums are well known to those of skill in the art and include, but are not limited to, phosphate buffered saline, distilled water, ethanol, polyol, DMSO, oils, detergents suspending agents or suitable mixtures thereof Other objects and advantages of the invention will become apparent to those skilled in the art from the accompanying description of the invention.

BRIEF DESCRIPTION OF THE DRAWINGS

FIG. 2A depicts Southern blot analysis of peritoneal exudate cells (PEC) and spleen cells from four representative lethally-irradiated mice reconstituted with $15 \times 10^6$ N2-infected T cell-depleted spleen target cells six and nine months earlier. Genomic DNA was prepared from spleen and PEC twenty-four and ninety-six hours after injection of thioglycollate and digested with the restriction enzyme Sac I and probed using a neo-specific probe. Lanes 1 and 3 represent DNA from granulocytes (twenty-four hours) and lanes 2 and 4 represent DNA from macrophages (ninety-six hours) as indicated by the lettering below the lanes. The last four lanes represent Sac I-digested pN2 plasmid DNA equivalent to 0.5, 1.0, from J11d-treated spleen cells (lanes 9,10) taken from the same mice used for harvesting PEC. FIG. 2B is a Southern blot showing genomic DNA extracted from PEC or spleen cells taken from three representative secondary mice previously reconstituted with $8 \times 10^6$ N2-infected, B and T cell-depleted, BM or spleen cells obtained from primary recipients were analyzed by Southern blotting. Lanes 1 and 2 represent DNA from macrophages (ninety-six hours PEC) taken from mice reconstituted with BM cells from positive primary mice. Lane 3 represents DNA from macrophages (96 hours PEC) taken from a mouse reconstituted with spleen cells from a positive primary mouse. Lanes 4–6 represent the same mice except that the DNA was extracted from spleen rather than PEC. The last four lanes represent Sac I-digested pN2 plasmid DNA equivalent to 0.5, 1.0, 2.0 and 5.0 copies/cell, respectively. FIG. 2C shows genomic DNA extracted from PEC, spleen or thymus harvested from mice reconstituted 4 months earlier with $8 \times 10^6$ N2-infected, T cell-depleted BM taken from syngeneic, C57Bl/6 μ knockout mice. Lanes 1 and 2 and 3 represent DNA from macrophages (96 hours PEC), spleen, and thymus respectively. Lanes 4–7 represent Sac I-digested pN2 plasmid DNA equivalent to 0.125, 0.25, 0.5 and 1.0 copies/cell, respectively.

DETAILED DESCRIPTION OF THE INVENTION

Figure 1:
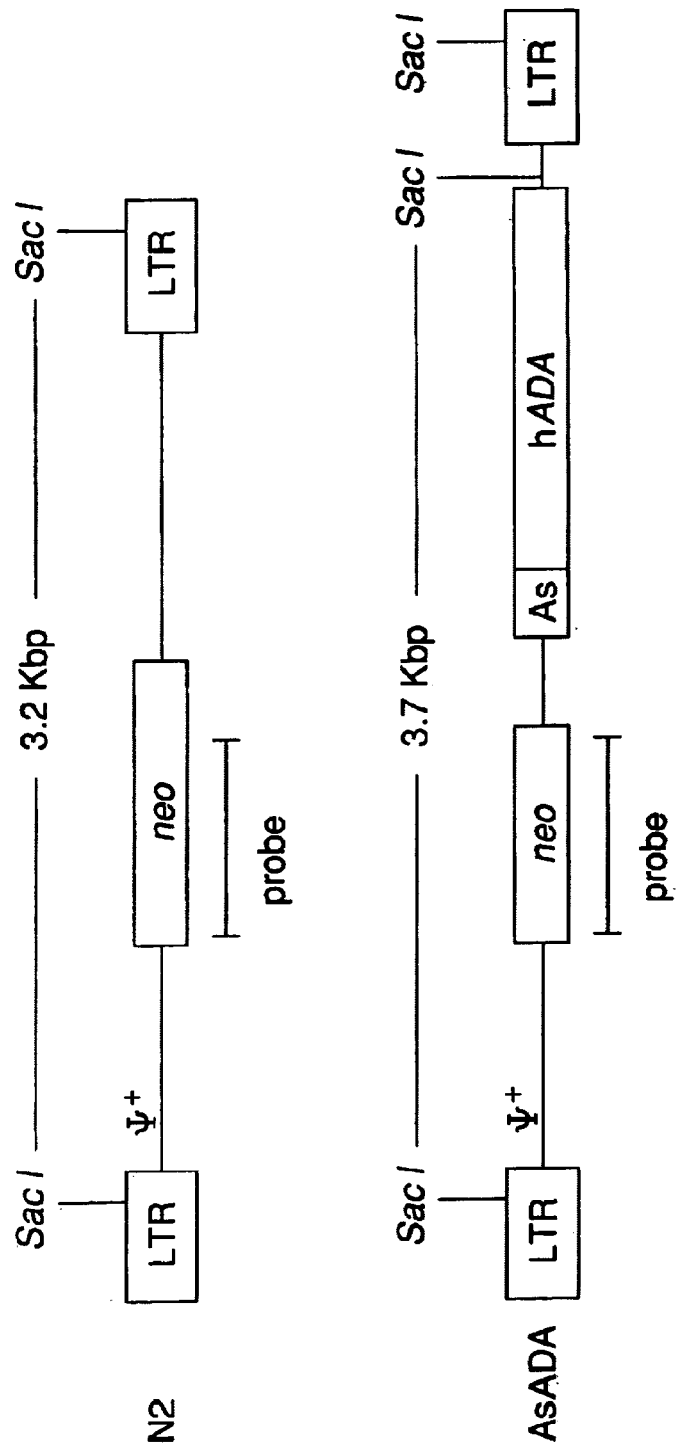
FIG. 1 shows schematic diagrams of the retroviral vectors used in gene transfer. Retroviral vectors N2 and AsADA are Moloney murine leukemia virus-based vectors. N2 contains the neomycin phosphotransferase gene (neo), expressed from the viral long terminal repeat (LTR) promoter. AsADA contains neo, expressed from the viral LTR promoter, and the human ADA gene, expressed from its endogenous promoter, As. Relevant restriction enzyme sites and the distance between them are indicated. A+ represents the packaging signal. The 930 bp Eag I-Ava I fragment in the neo coding region was used as a probe in experiments described in Figure legends 2 and 3.

Mammalian hematopoietic (blood) cells provide a diverse range of physiologic activities. Hematopoietic cells are divided into lymphoid, myeloid and erythroid lineages. The lymphoid lineage, comprising B, T and natural killer (NK) cells, provides for the production of antibodies, regulation of the cellular immune system, detection of foreign agents in the blood, detection of cells foreign to the host, and the like. The myeloid lineage, which includes monocytes, granulocytes, megakaryocytes, as well as other cells, monitors for the presence of foreign bodies, provides protection against neoplastic cells, scavenges foreign materials, produces platelets, and the like. The erythroid lineage provides the red blood cells, which act as oxygen carriers.

A spleen-residing, long-lived myeloid-committed stem cell population is provided in accordance with the present invention. Also provided are methods for isolating such cells and vectors suitable for introducing exogenous genes into these myeloid-committed stem cells. Myeloid cells so transduced, continuously replenish the myeloid lineage and may be used to advantage for gene therapy based treatment of genetic disorders inherent to the myeloid lineage.

More than 40 different lysosomal storage diseases have been identified in humans, each resulting from a deficiency in one of the many enzymes involved in the breakdown of macromolecules. Descriptions of several of these genetic diseases are provided hereinbelow.

Gaucher disease is the most prevalent lysosomal storage disease and has its highest incidence in the Ashkenazi Jewish population. Over 100 mutant alleles have been identified in affected patients, but four alleles, termed N370S, L444P, 84GG, and IVS2, have significant frequencies in this population. The disease results from glycocerebroside accumulation due to a genetic deficiency in glucocerebrosidase.

Tay-Sachs disease (TSD) is an autosomal-recessive, progressive, and ultimately fatal neurodegenerative disorder. Within the last 30 years, the discovery of the enzymatic basis of this disease, namely deficiency of the enzyme hexosaminidase A, made possible both enzymatic diagnosis of TSD and heterozygote identification. In the last decade, the cloning of the HEXA gene and the identification of more than 80 associated TSD-causing mutations has permitted molecular diagnosis in many instances. The availability of the nucleic acid sequence encoding hexoaminidase A provides the basis for constructing retroviral vectors encoding this enzyme for the treatment of Tay Sachs disease.

Hunter syndrome is a rare, X-linked, recessively inherited disease affecting approximately 1 in 132,000 males. The disease is caused by the inability to degrade dermatan sulphate and heparan sulphate due to mutations in the iduronate-2-sulphatase gene (IDS). The mutations causing the disorder are heterogeneous, ranging from small microlesions to gross deletions and inversions. Again the availability of the nucleic acid sequence encoding iduronate-2-sulphatase facilitates the development of therapeutic vectors for the treatment of this disorder.

Hurlers syndrome is a mucopolysaccharidosis in which there is a deficiency of α-L-iduronidase. Symptoms include an accumulation of an abnormal intracellular material, severe abnormality in the development of skeletal cartilage and bone with dwarfism, kyphosis, deformed limbs, limitation of joint motion, corneal clouding and mental retardation.

Niemann-Pick Disease (NPD) is an autosomal recessive lysosomal storage disorder caused by a deficiency of acid sphingomyelinase (ASM). NPD occurs in two forms, neuronopathic Type A and normeuronopathic Type B. The incidence of Type A NPD is highest among Ashkenazi Jews. Type B NPD is more common in non-Jews but has been reported in Ashkenazi Jews. As with the disorders described above, the ASM sequence has been determined and thus construction of therapeutic vectors encoding this enzyme are contemplated to be within the scope of the present invention.

Arylsulfatase A (ARSA) deficiency is the main cause of metachromatic leukodystrophy (MLD), a lysosomal disorder with no specific treatment. Accordingly, therapeutic intervention utilizing the vectors and methods of the present invention should provide an effective means for treating MLD.

Other lysosomal storage diseases that may be treated using the vectors and methods of the present invention include, but are not limited to, Pompe disease, Krabbe disease, Fucosidosis, Mannosidosis, Farber disease, and Glucosaminuria.

In one aspect of the invention, LPS-stimulated, T cell-depleted spleen cells were infected with a retroviral vector containing the neomycin phosphotransferase (neo) marker gene and were used to rescue lethally-irradiated syngeneic recipients. 0.5–1 copy per cell of the neo gene could be detected by Southern blotting in thioglycollate induced granulocytes and macrophages for at least 12 months after reconstitution. In situ PCR revealed the presence of the gene in greater than 80% of induced granulocytes and macrophages in the peritoneal cavity twelve months after adoptive transfer. The targeted stem cell in the spleen was not a self-renewing PSC since secondary, lethally irradiated recipients reconstituted with BM taken from primary recipients never expressed the exogenous gene in myeloid cells or in any other cell type. Further indication that PSC were not targeted was the fact that the lymphoid lineage (T cells and most B cells) were invariably negative. Since the average life of mature granulocytes and macrophages is around two weeks (17) and that of granulocytes is only a few days (18), these results indicate that the targeted lineage-committed stem cell population was the main replenishing source for the myeloid lineage for at least twelve months. Based on these results and the previous studies cited above, the splenic cells targeted in these experiments are classified as earlier myeloid precursors than CFU-S cells.

The following protocols are provide to facilitate the practice of the present invention.

Mice

C57Bl/6, (BALB/C×C57Bl/6)F1 and B cell deficient (μknockout) C57Bl/6 male[19] and female mice were purchased from the Jackson Laboratory (Bar Harbor, Me.).

Retroviral Vectors and Virus-Producing Cell Line pN2[20] (a gift from E. Gilboa) and pAsADA (FIG. 1) are Moloney murine leukemia virus (MLV)-based retroviral vectors that contain the neomycin phosphotransferase (neo) gene, which is expressed from the MLV long terminal repeat (LTR) promoter. pAsADA (provided by Gene Therapy, Inc.) contained in addition to the neo gene, the human adenosine deaminase (ADA) gene driven by its own minimal promoter[21]. N2 and AsADA virus producing cells were previously described[22]. Briefly, the NIH 3T3-based ecotropic murine packaging cell line GP+E-86[23] were transfected with 5 μg of pN2 or pAsADA retroviral vectors using the polybrene/DMSO shock method, followed by selection with G418 (0.35 mg/ml, GIBCO-BRL, Grand Island, N.Y.). The retroviral titer for both virus producing cell lines ranged from $1.5–2.0 \times 10^7$ colony forming units per ml.

Gene Transfer

The gene transfer protocol was performed as follows: enriched B cell populations were prepared from the spleens of C57Bl/6, (BALB/C×C57Bl/6)F1 or B cell deficient (μknockout) C57Bl/6 mice by depleting T cells with mAb J1j, (rat IgM anti-mouse Thy-1.2)[24], plus complement treatment. The remaining cells were stimulated for 24 hours with 50 μg/ml LPS and then cocultivated with a monolayer of irradiated (1,600R)N$_2$ or AsADA virus producing cells in the presence of 6 μg/ml polybrene. The non-adherent cells were collected and washed 24 hours later, and 4 to $15 \times 10^6$ of the cells were injected i.v into each lethally irradiated (1000R) (BALB/C×C57Bl/6)F1 recipient mouse.

Cell preparation, Southern blotting analysis and ADA assay. Thioglycollate was injected i.p. 24 or 96 hr prior to the isolation of myeloid cells to induce the recruitment of granulocytes and macrophages to the peritoneum of the reconstituted recipients. Some of the peritoneal exudate cells (PEC) were fixed onto glass slides for in situ PCR and hybridization as described below. Spleen cells were isolated from the same mice from which the PEC were isolated. Part of the spleen cells were injected into the lethally irradiated secondary recipient mice and some of the spleen cells were treated with the monoclonal antibody J11d (rat IgM anti mouse heat stable antigen)[24] or J1j and complement prior to the extraction of genomic DNA, followed by Southern blotting or ADA assay. Southern blotting was performed according to standard procedures. For detection of the neo marker gene, 10 µg/lane of Sac I digested genomic DNA were screened using a $^{32}$p-labeled probe, an Eag I-Ava I fragment from the neo coding region. To determine the clonality of the transduced population, 10 µg/lane of BamH I or Hind III digested genomic DNA were screened using the same probe as above.

The ADA assay was described previously[22]. Briefly, $1 \times 10^6$ target cells were lysed by multiple freezing/thawing cycles, and samples were separated by electrophoresis on cellulose acetate plates. Enzyme activity was developed by an agar overlay containing adenosine, nucleoside phosphorylase, xanthine oxidase, phenazine methosulfate, and dimethylthiazol diphenylterazolium bromide.

In Situ PCR and Hybridization

PEC were fixed onto glass slides with 4% paraformaldehyde, washed and dehydrated. The cells were then permeabilized with proteinase K and sealed with the PCR mixture containing the neo specific primers 5'-CAGGATGATCTGGACGA (SEQ ID NO:1) and 3'-TGGATGCCGACGGATTTGCA (SEQ ID NO:2). Cycling conditions were 94° C., 1 min., 55° C., 1 min., 72° C., 1 min. 30 sec., for 30 cycles. After the PCR reaction was completed, the slides were washed and incubated with the hybridization mixture containing a 404 bp neo-specific biotinylated probe complementary to the PCR amplified sequence excluding the primer region. Streptavidin was then added (to amplify the signal) followed by biotin-conjugated alkaline phosphatase. Color was developed using BCIP/NBT[25]. The cells were analyzed on a Bright-field phase, differential interference contrast microscope. Images were captured using a Dage CCD72 camera and Dage DSP2000 digital signal processor (capable of on-chip integration for low-light situations), and a MACINTOSH QUADRA® 700 with a Scion LG-3 frame grabber board.

The following examples are provided to illustrate preferred embodiments of the invention. The embodiments described below are in no way intended to limited the scope of the invention Example I Retrovirus-Mediated Gene Tagging of a Long-Lived Myeloid Precursor Population in the Spleen Efficient gene transfer protocols for the introduction of exogenous genes into highly purified lymph node (LN) B and T cells have been developed for various purposes[22,26,27]. During the course of these experiments, we observed that when T cell-depleted spleen cells (rather than LN cells) were used as the target cells in this system, cells harboring the exogenous gene could also be detected in non-lymphoid tissues such as liver and lungs as well as in spleen and LN and in some experiments, in low levels also in the thymus (data not shown). Since signals were obtained from organs that normally do not contain significant numbers of B cells, this raised the possibility that some spleen-residing stem cells were also targeted and gave rise to tissue residing myeloid cells.

To assess this possibility, thioglycollate-induced, granulocytes and macrophages harvested from animals reconstituted with retroviral vector targeted BM cells were directly assayed for the presence and expression of an exogenous gene introduced by the retroviral vector.

Figure 2A:
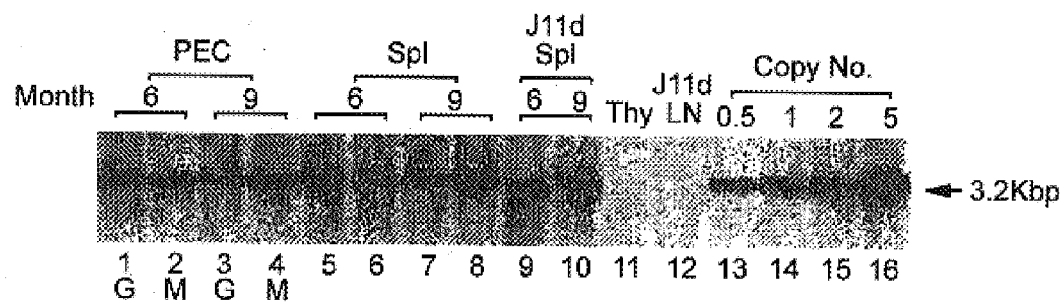
FIGS. 2A, 2B and 2C are Southern blots showing gene transfer into the myeloid lineage but not pluripotential hematopoietic stem cells.

LPS-stimulated, T cell-depleted spleen cells taken from (BALB/c×C57Bl/6)F1 or C57Bl/6 mice were infected by cocultivation with packaging cell line producing the N2 vector virus (FIG. 1) and adoptively transferred into lethally irradiated F1 recipients. Gene transduction was dependent upon LPS stimulation but independent of T cell depletion although T cell depletion results in a higher transduction efficiency (data not shown). A total of 30 recipient mice were injected with thioglycollate 6–9 months after adoptive transfer to induce granulocyte and macrophage migration into the peritoneal cavity. As assessed by α-naphthyl acetate esterase staining (macrophage-specific) versus naphthol AS-D chloroacetate esterase staining (granulocyte-specific), 24 hours after injection of thioglycollate, greater than 95% of the cells harvested from the peritoneum were granulocytes, whereas 96 hours after thioglycollate injection, greater than 95% of the cells were macrophages (data not shown). Six and nine months post transfer, approximately 1.0–2.0 proviral copies per cell were detected in both peritoneal granulocytes and macrophages by Southern blotting (FIG. 2A). DNA extracted from granulocytes (24 hours PEC) was analyzed in lanes 1 and 3 at 6 and 9 months post reconstitution, respectively (FIG. 2A). Lanes 2 and 4 show the same analysis but for macrophages (96 hours PEC). Lanes 5–8 represent DNA from the spleens of the same animals. Lanes 9 and 10 represent DNA from the same spleen cells used in lanes 5 and 8, respectively, but after treatment with the monoclonal antibody J11d and complement. J11d is a cytotoxic antibody specific for the murine heat stable antigen (HSA). It removes 80–90% of splenic B cells but spares macrophages. The results indicate that in this experiment, approximately half of the signal (as measured by gel densitometry) obtained from the spleens was due to resident macrophages.

The donor origin of the hematopoietic system in the target animals was verified by flow cytometric analysis of both macrophages and B cells in recipient F1 mice reconstituted with parental C57Bl/6 target cells using MHC class I and II-specific antibodies. The degree of chimerism was checked directly on PEC with an anti-H-2D$^d$ antibody and on spleen cells with MHC class II-specific anti-I-E$^{k,d}$ antibodies. C57Bl/6 do not express I–E and therefore spleen cells from a C57Bl/6–(C57Bl/6×BALB/c)F1 should not stain with this antibody. FIG. 3 clearly indicates that the myeloid and lymphoid (B cells) lineages in the reconstituted animals were derived entirely from donor stem cells (H-2$^+$, I-E$^-$). Taken together, these results indicate a very efficient infection of a precursor cell population which contributes to the myeloid lineage for at least 9 months.

Pluripotential Hematopoietic Stem Cells Were Not Infected During Gene Transfer.

Figure 2B:
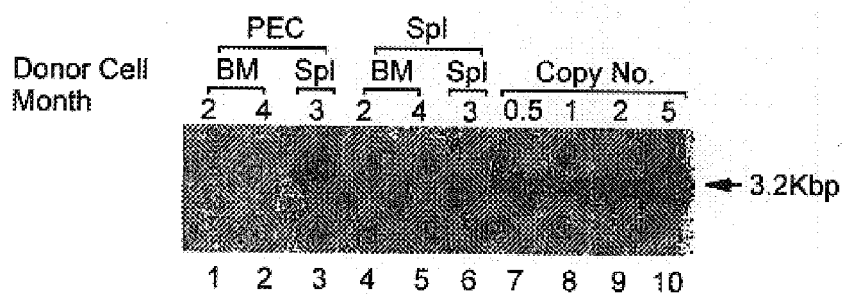

The next set of experiments were performed to determine the type of progenitor cells that were successfully transduced using the methods and compositions of the invention; i.e., whether pluripotential hematopoietic stem cells as opposed to rather later stage, lineage-committed progenitor cells were targeted. Two assumptions could be made if pluripotential cells were targeted in the initial inoculum. The first is that all hematopoietic lineages in the reconstituted animals should harbor the marker gene. This was not the case in any of the mice tested. Southern blots were always negative for the marker genes in B cell-depleted LN (FIG. 2A, lane 12), and in most experiments was also undetected in thymus (FIG. 2A, lane 11). In some experiments, a weak signal can be detected in the thymus (FIG. 2C, lane 3) which is not surprising since this organ does contain a small fraction of BM-derived macrophages. The second is that BM cells from the reconstituted animals should be able to transfer the marker gene into a secondary lethally irradiated host. To test this, BM or spleen cells from positive primary recipients were used to reconstitute secondary lethally-irradiated recipients. To ensure that the cells transferred into secondary recipients were depleted of mature B cells that might contain the exogenous gene, donor BM cells were first treated with Jild and complement (to remove B cells) and also with Jlj (anti-Thy-1 monoclonal antibodies, to remove mature T cells) and complement. Over 30 secondary recipients reconstituted with BM taken from primary positive mice were examined and proviral sequences were never detected by Southern blotting in 96 hours PEC (FIG. 2B, lanes 1 and 2) and spleen (FIG. 2B, lanes 4 and 5).

In contrast to BM, the spleen should contain the targeted myeloid precursor cells and therefore, in parallel, secondary irradiated animals were reconstituted with $8 \times 10^6$ B and T cell-depleted spleen cells taken from positive primary reconstituted mice. In these experiments, all secondary recipients were positive for proviral sequences both in 96 hours PEC (FIG. 2B, lane 3) and in spleen (FIG. 2B, lane 6). The signals are weaker here (0.1–0.4 copies per cell for PEC) probably because only $8 \times 10^6$ spleen cells were transferred, however, all 6 mice tested were positive. T cells isolated from spleen, LN and thymus of these mice (secondary recipients) were invariably negative (data not shown). These results strongly suggest that pluripotential stem cells were not targeted during the first infection.

Figure 2C:
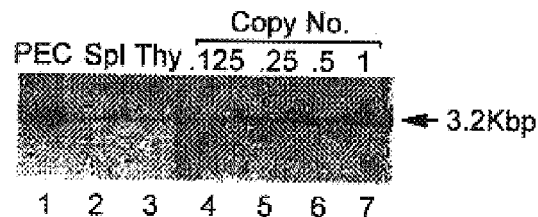
Figure 3A:
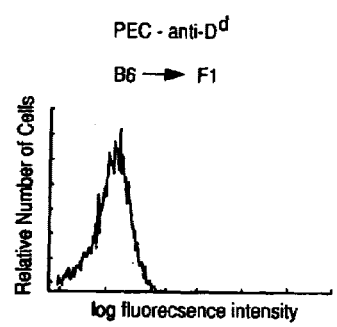
FIGS. 3A–3D are histograms showing the results of FACS analysis revealing that myeloid and B cells in C57Bl/6–(BALB/c×C56Bl/6)F1 chimeras are of donor origin. Five day peritoneal exudate cells (PEC) and spleen cells taken from C57Bl/6–(BALB/c×C56Bl/6)F1 or (BALB/c×C56Bl/6)F1 were stained with FITC labelled 34-4-21S (anti-$D^d$) and 14-4-4 (anti-1-$E^{k,d}$) antibodies respectively and analyzed by FACS.
Figure 3C:
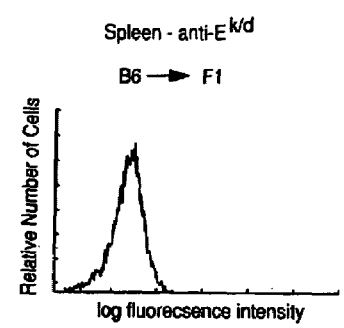
Figure 3B:
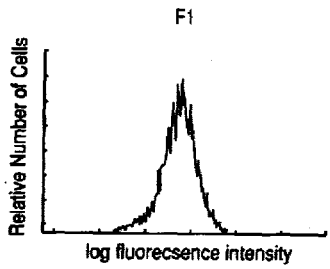
Figure 3D:
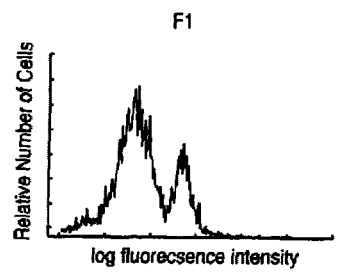

Since the infection protocol using LPS-activated, T cell-depleted spleen cells as target cells results in the transduction of both myeloid precursors and mature B cells, the next set of experiments were designed to rule out the possibility that some of the signal is due to residual B cells. In these experiments, spleen cells taken from B cell-deficient mice (μ knockout mice) were used as target cells. In this case no infected B cells are transferred and the donor stem cells cannot generate any B cells and therefore the recipient animals were totally devoid of donor origin B cells. As seen in FIG. 2C, PEC taken from such mice 4 months after cell transfer contained an average of one copy per cell of the exogenous gene similar to the results obtained with normal spleen (FIG. 2A). Spleen cells contained an average of 0.125 copies per cell which is, as expected, much lower than when normal spleen cells were used as target cells since in this case there are no infected B cells in the inoculum. Very faint band could be seen from thymocytes upon overexposure.

Absence of Replication-Competent Virus in Reconstituted Recipients

Figure 4:
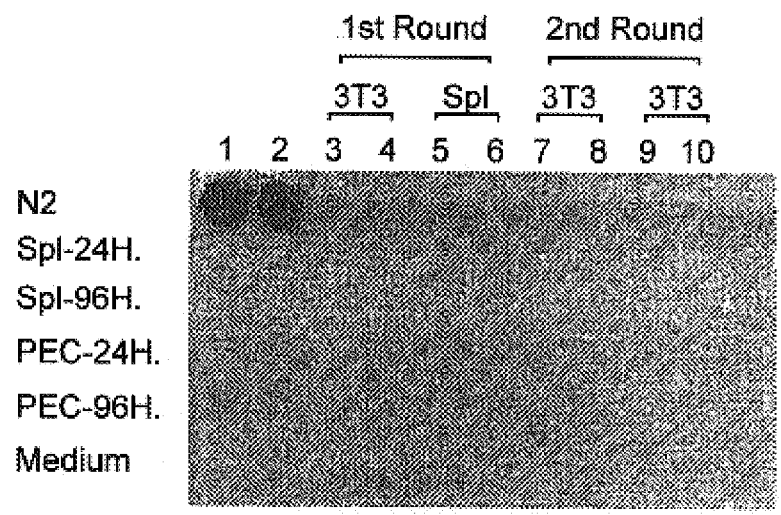
FIG. 4 is a blot showing the results from a reverse transcriptase assay for the detection of replication competent virus. PEC and spleen cells were obtained 24 and 48 hours after thioglycollate injection and co-cultured with either 3T3 cells or LPS-stimulated spleen cells. Supernatants were obtained every 24 hours for 7 days and added to fresh 3T3 cells. Two samples of supernatants harvested at day 3 of the first and second cultures were checked for the presence of RT (columns 3–10). Columns 1 and 2 represent control supernatants taken from cultures of N2 producer line, spleen cells, PEC and media control, as marked in the figure.

To rule out the possibility that the results reflect a lateral spread of vector virus due to activation of an endogenous retrovirus, assays were performed to determine whether replication-competent virus could be detected in PEC or LPS-stimulated spleen cells isolated from reconstituted mice 24 or 96 hours after thioglycollate injection. $1 \times 10^6$ PEC or spleen cells were cocultivated with either $2 \times 10^5$ NIH 3T3 cells or $1 \times 10^6$ primary syngeneic spleen cells for 7 days. Supernatant was harvested from these cultures every 24 hours and tested for reverse transcriptase (RT) activity according to standard procedures[28]. If replication-competent virus was present, it should have been propagated in fresh cells, and supernatant from these cultures should be positive for RT activity. In parallel, each supernatant sample was added to fresh cultures of NIH 3T3 cells for a second round of expansion for an additional 7 days, and RT activity was also checked every 24 hours. FIG. 4 represents the results from supernatants taken from day 3 of the primary and secondary cultures, and as can be seen, all of the samples were negative except for the positive control. RT activity was negative for all time points tested. Moreover, the NIH 3T3 cultures from both rounds of amplification were also scored for transfer of the neo-containing N2 vector by selection with G418 (350 μg/ml). If replication-competent virus was present, it should provide viral proteins for passage of N2 vector virus. No G418-resistant colonies were detected (data not shown) providing additional support that replication-competent virus was not present in vector positive animals, ruling out horizontal spread of the vector virus due to activation of a latent endogenous retrovirus.

In Situ PCR of Peritoneal Exudate Cells

Figure 5A:
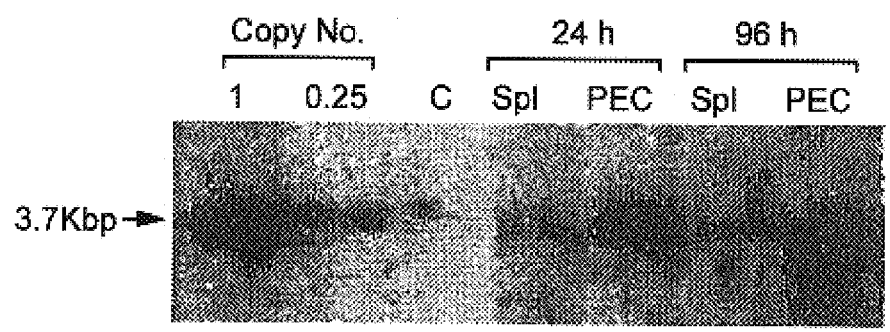
FIGS. 5A shows Southern blotting of genomic DNA prepared from PEC twenty-four and ninety-six hours after thioglycollate treatment and spleen from two representative mice reconstituted six months earlier with $20 \times 10^6$ cells of T cell-depleted spleen cells infected with pAsADA. DNA was digested with Sac I and probed with a neo-specific probe. Sac I digested pAsADA plasmid DNA equivalent to 0.25 and 1 copies/cell are as indicated.
Figure 6A:
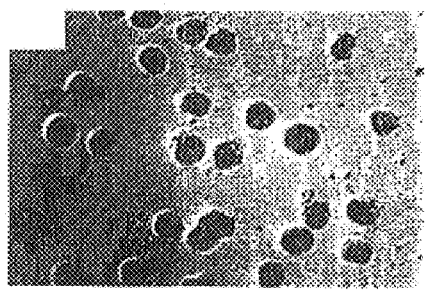
FIGS. 6A–6D are a series of micrographs showing detection of provirus sequences by in situ PCR amplification. Peritoneal granulocytes and macrophages were harvested twenty-four and ninety-six hours, respectively, after thioglycollate injection from control (FIGS. 6A and 6C) or from mice reconstituted with targeted spleen cells (FIGS. 6B and 6D) 12 months earlier and subjected to in situ PCR using biotinylated probes. Amplified neo-specific sequences were visualized on a cell per cell basis using an alkaline phosphatase-based colorimetric assay.
Figure 6C:
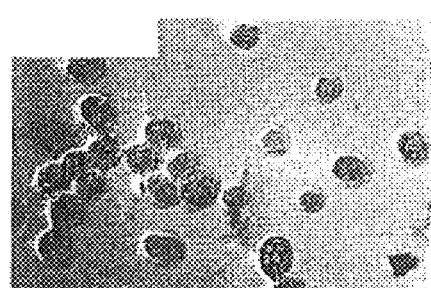
Figure 6B:
Figure 6D:
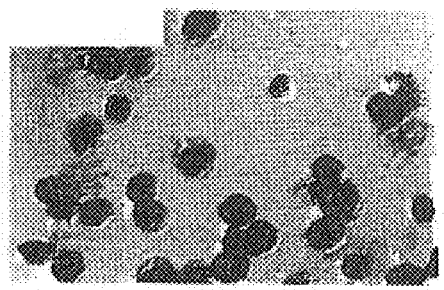

As shown in FIG. 5A, gene transfer into the myeloid lineage, as assessed by Southern blotting, was as efficient for the ADA gene as it was for the neo gene. However, the results obtained by Southern blotting can only indicate the average number of exogenous gene copies per cell. They cannot indicate whether most cells harbor one copy or whether a few cells harbor many copies of the gene. To determine the exact percentage of myeloid cells that harbor the transduced gene, in situ PCR was used to amplify the transduced neo gene followed by specific hybridization of biotinylated neo-specific probes. This allows the visualization of positive signals and the morphology of the target cell on a cell per cell basis. At least 80% of both granulocytes (FIG. 6C) and macrophages (FIG. 6D) from reconstituted animals harbored at least one copy of the transduced neo gene. Cells from control animals were totally negative (FIGS. 6A and 6A).

Clonal Analysis of the Targeted Myeloid Population

Figure 7:
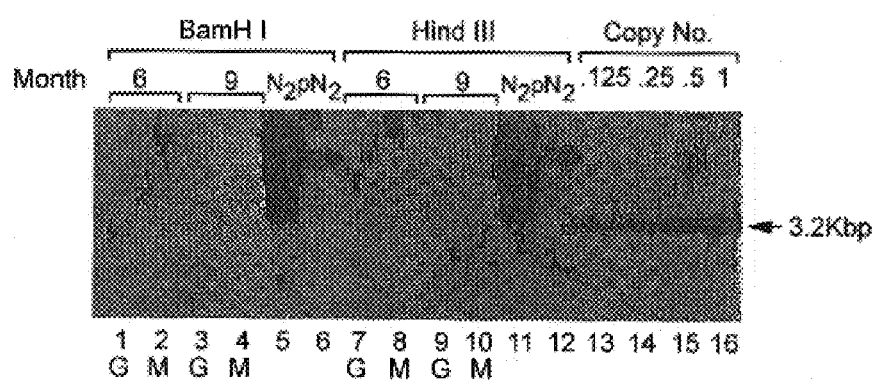
FIG. 7 is a Southern blot showing the results from a clonal analysis of the populations of PEC derived granulocytes and macrophages. The PEC isolated from the same mice described in FIG. 2A were used for clonal analysis. Genomic DNA was prepared from PEC twenty-four and ninety-six hours after injection of thioglycollate and digested with the restriction enzyme Bam HI or Hind III and probed using a neo-specific probe. Lanes 1,3,7, and 9 represent DNA from granulocytes (twenty-four hours) and lanes 2, 4, 8, and 10 represent DNA from macrophages (ninety-six hours) as indicated by the lettering below the lanes. Genomic DNA from the $N_2$ producer cell, (lanes 5 and 11) and one copy of plasmid DNA, $pN_2$ (lanes 6 and 12) were used for oligoclonal and monoclonal controls respectively. The last four lanes represent Sac I-digested $pN_2$ plasmid DNA equivalent to 0.125, 0.25, 0.5, and 1.0 copies/cell, respectively.

Previous retroviral gene tagging of pluripotential stem cells suggested that at any particular time point, very few clones contribute to the generation of the various hematopoietic lineages[31,32]. To test the degree of clonality in the mature myeloid lineage after adoptive transfer of retrovirus-tagged spleen cells, the same DNA used in the Southern blotting analysis for the detection of the proviral DNA in PEC-derived granulocytes and macrophages was digested with either BamH I or Hind III. These enzymes cut once within the retroviral vector. Therefore, if the mature PEC arise from one or few precursor clones, one would expect to see only a few bands in a Southern blot when neo-specific probes are used. The results shown in FIG. 7 clearly demonstrate that the populations of peritoneal granulocytes and macrophages are not oligoclonal. Discrete bands were not detected in the Southern blot analysis after exposure for one to two days even though the blot was sensitive to below 0.125 copies of the exogenous gene per cell. After longer exposure, some faint bands (corresponding to 0.001 copies per cell) could be detected which might suggest that some infected clones contribute a little more than others to the mature myeloid population.

Evidence is presented for the existence of a long-lived, spleen residing, myeloid-committed stem cell population. These stem cells can be targeted with a retroviral vector after stimulation of T cell-depleted spleen cells with LPS. Since current retroviral vectors, including the ones used in this study require at least one round of cell replication in order to integrate into the cell's genome, the targeted stem cells are induced to proliferate either directly or indirectly by LPS. There was no gene transduction in the absence of LPS however, transduction was independent upon the presence of B cells since spleen cells from B cell-deficient (μ knockout) mice were as efficiently transduced as normal B cells. This suggests that the targeted cells themselves are responsive to LPS. The evidence that this cell population is not pluripotential is three-fold. First, the targeted cells do not home back to the BM and therefore, secondary BM transfers from positive mice into normal irradiated recipients do not transfer the exogenous gene. Second, whereas at least 80% of mature thioglycollate-induced granulocytes and macrophages were positive for the exogenous gene, as determined by in situ PCR, newly generated T and B lymphocytes were not. Third, clonal analysis of the targeted macrophages and granulocytes populations (FIG. 7) indicated that the cells were not of oligoclonal origin which should have been the case if pluripotential cells were targeted[14,15]. However, it is not clear how homogenous the targeted stem cell population is and it can represent either a pan myeloid stem cell population or a pool of more than one precursor cells such as macrophage and granulocyte-committed stem cells.

Surprisingly, these myeloid-committed stem cells contributed to the replenishment of the mature myeloid population for at least 9 months, as assessed Southern blot analysis and for 12 months as assessed by in situ PCR and. Their ability to replenish the mature myeloid cell populations for prolonged periods is seemingly antithetical to the current dogma that cells other than PSC contribute to the hematopoietic lineage for a limited period only. This dogma, however, is based on studies using BM cell transfers and our findings are based on spleen cell transfers. It is therefore possible that the targeted population we describe only resides in the spleen. It is equally plausible that this population is present in BM but co-purifies with the enriched BM population that contains pluripotential cells. Only 10% of this population are PSC and the rest of the cells are at present not well characterized The myeloid precursor(s) we describe might be part of the uncharacterized fraction of this population. If these myeloid precursor cells also reside in BM, why were they not detected by others is unclear. One possibility could be that they do not respond to any of the stimuli used by others and would have been detected if LPS was used. This possibility is currently under investigation.

Aside from the implication these findings have on our understanding of hematopoiesis, the ability to specifically introduce exogenous genes into the myeloid lineage offers an opportunity to study the consequences of expressing an exogenous gene exclusively in the myeloid lineage using somatic cell gene transfer. So far, retroviral-mediated gene transfer into the myeloid lineage has mainly been achieved by the transduction of BM stem cells and the efficiency was rarely higher than 5%[33]. Other disadvantages of using BM cells is that 1) PSC comprise a rare population in BM; 2) PSC are difficult to purify; 3) PSC do not provide ideal targets for gene transfer; and 4) PSC are not lineage-specific. Even if the efficiency of gene transfer into pluripotential cells improves in the future, transduction of exogenous genes into these cells would probably result in the expression of the gene in all hematopoietic cell lineages which may not always be desirable. In contrast, transduction of myeloid-committed stem cells as described herein allows specific expression in the myeloid compartment. This cell would therefore make a more suitable target for gene therapy-based treatment of genetic disorders inherent to the myeloid lineage such as Gaucher's disease.

Example II

Figure 8:
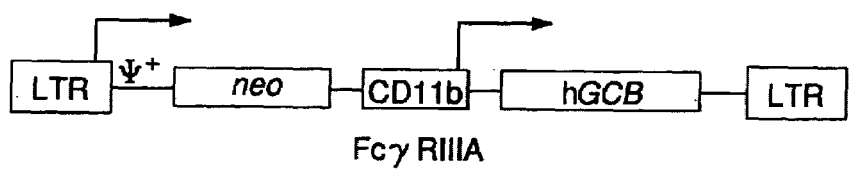
FIG. 8 is a schematic diagram of an exemplary therapeutic vector suitable for the treatment of Gauchers disease. The genebank accession number for the glucocerebrosidase gene is provided.

Gene Therapy Methods for Introducing Nucleic Acids Encoding Beneficial Proteins into Stem Cells of the Myeloid Lineage FIG. 8 shows an exemplary vector for correcting the genetic defect in the glucocerebrosidase gene observed in Gauchers disease. Spleen cells will be isolated from a test subject, preferably by biopsy. The biopsy plugs will be either enzymatically or mechanically treated to generate a single cell suspensions. Such methods are well known to those of ordinary skill in the art. Enriched B cell populations will be prepared from the spleen biopsies by depleting T cells with monoclonal antibodies specific for T cell markers plus complement treatment. The remaining cells will be stimulated for 24 hours by LPS and then co-cultivated with a monolayer of irradiated therapeutic retroviral virus producing cells in the presence of polybrene. In this example, the vector depicted in FIG. 8 will be utilized. The non-adherent cells will be collected and washed 24 hours later and the glucocerebrosidase producing myeloid-specific stem cells will be injected into the test subject from which the cells were derived. The patient will then be assessed at appropriate time intervals for alleviation of symptoms associated with Gauchers disease. Glucocerebrosidase levels will also be assessed over time.

While this example describes vectors and methods for the treatment of Gauchers disease, as mentioned previously, there are a plethora of lysosomal storage related diseases, most associated with a point mutation in genes critical for macromolecule degradation. Accordingly, once a mutated gene has been identified as the underlying cause of a particular disorder, the vectors and methods of the invention may be adapted for the treatment of that particular disorder.

Example III

Potentiation of Immune Responses

Another potential use of myeloid-specific stem cell targeting is based on the fact that macrophages and dendritic cells which both belong to the myeloid lineage are two of the major antigen producing cells (APC) in the immune system. It is well established that initiation of T cell mediated immune responses are dependent upon antigen presentation by APC. Antigen presentation is a process that involves the enzymatic degradation of long proteins into small peptides which bind to the major histocompatibility (MHC) molecules and anchor as a complex on the outer membrean of APC. We have developed several retroviral vectors that contain genes that are fused to the necessary sequences that target the exogenous gene into the appropriate cellular compartment where MHC coupling occurs. Methods and vectors are exemplified in U.S. Pat. No. 5,686,280, the disclosure of which is incorporated herein by reference. We can therefore, create an immunogenic form of a protein which is specifically expressed in the myeloid compartment. This approach can be used to activate the immune system against specific viral and/or tumor antigens. It can be used for induction of a prophylactic immune response as well as a specific immune response against an existing pathogen or tumor. Currently identified tumor antigens useful for this purpose include, but are not limited to MAGE1 and MAGE3, tyrosinase, p21 Ras, CEA, Lewis, CD44, mut EGFR, EBNA-1, CD10, PSA, p53, BCR-able and mucin.

REFERENCES

1. Metcalf D, Moore M S: Anonymous Haemopoietic Cells, New York, Elsevier, 1971, p 1
2. Morrison S J, Uchida N, Weissman I L: The biology of hematopoietic stem cells. Annual Review of Cell & Developmental Biology 11:35, 1995
3. Spangrude G J, Heimfeld S, Weissman I L: Purification and characterization of mouse hematopoietic stem cells. Science 241:58, 1988

4. Suda T, Suda J, ogawa M: Single-cell origin of mouse hemopoietic colonies expressing multiple lineages in variable combinations. Proc Natl Acad Sci USA 80:6689, 1983

5. Visser J W, Bauman J G, Mulder A H, Eliason J F, de Leeuw A M: Isolation of murine pluripotent hemopoietic stem cells. J Exp Med 159:1576, 1984

6. Morrison S J, Weissman I L: The long-term repopulating subset of hematopoietic stem cells is deterministic and isolatable by phenotype. Immunity 1:661, 1994

7. Spangrude G J, Brooks D M, Tumas D B: Long-term repopulation of irradiated mice with limiting numbers of purified hematopoietic stem cells: in vivo expansion of stem cell phenotype but not function. Blood 85:1006, 1995

8. Uchida N, Weissman I L: Searching for hematopoietic stem cells: evidence that Thy-1.1lo Lin- Sca-1+ cells are the only stem cells in C57BL/Ka-Thy-1.1 bone marrow. J Exp Med 175:175, 1992

9. Till J E, McCulloch E A: A direct measurement of the radiation sensitivity of normal mouse bone marrow cells. Radiation Research 14:213–222, 1961

10. Magli M C, Iscove N N, Odartchenko N: Transient nature of early haematopoietic spleen colonies. Nature 295:527, 1982

11. Bertoncello I, Hodgson G S, Bradley T R: Multiparameter analysis of transplantable hemopoietic stem cells. II. Stem cells of long-term bone marrow-reconstituted recipients. Exp Hematol 16:245, 1988

12. van der Loo J C, van den Bos C, Baert M R, Wagemaker G, Ploemacher R E: Stable multilineage hematopoietic chimerism in alpha-thalassemic mice induced by a bone marrow subpopulation that excludes the majority of day-12 spleen colony-forming units. Blood 83:1769, 1994

13. Morrison S J, Wright D E, Cheshier S H, Weissman I L: Hematopoietic stem cells: challenges to expectations. Curr Opin Immunol 9:216, 1997

14. Keller G: Hematopoietic stem cells. Curr Opin Immunol 4:133, 1992

15. Lemischka I R: What we have learned from retroviral marking of hematopoietic stem cells. Curr Top Microbiol Immunol 177:59–71:59, 1992

16. Harrison D E, Jordan C T, Zhong R K, Astle C M: Primitive hemopoietic stem cells: direct assay of most productive populations by competitive repopulation with simple binomial, correlation and covariance calculations. Exp Hematol 21:206, 1993

17. Ron Y, Lo D, Sprent J: T cell specificity in twice-irradiated F1—parent bone marrow chimeras: failure to detect a role for immigrant marrow-derived cells in imprinting intrathymic H-2 restriction. Journal of Immunology 137:1764, 1986

18. Lagasse E, Weissman I L: bcl-2 inhibits apoptosis of neutrophils but not their engulfment by macrophages. J Exp Med 179:1047, 1994

19. Kitamura D, Roes J, Kuhn R, Rajewsky K: A B cell-deficient mouse by targeted disruption of the membrane exon of the immunoglobulin mu chain gene. Nature 350: 423, 1991

20. Armentano D, Yu S F, Kantoff P W, von Ruden T, Anderson W F, Gilboa E: Effect of internal viral sequences on the utility of retroviral vectors. J Virol 61:1647, 1987

21. Valerio D, Duyvesteyn M G, Dekker B M, Weeda G, Berkvens T M, van der Voorn L, van Ormondt H, van der Eb A J: Adenosine deaminase: characterization and expression of a gene with a remarkable promoter. EMBO J. 4:437, 1985

22. Kuo M L, Sutkowski N, Ron Y, Dougherty J P: Efficient gene transfer into primary murine lymphocytes obviating the need for drug selection. Blood 82:845, 1993

23. Markowitz D, Goff S, Bank A: A safe packaging line for gene transfer: separating viral genes on two different plasmids. Journal of Virology 62:1120, 1988

24. Bruce J, Symington F W, McKearn TJ, Sprent J: A monoclonal antibody discriminating between subsets of T and B cells. J Immunol 127:2496, 1981

25. Bagasra O, Seshamma T, Pomerantz F: in situ PCR and Hybridization to Detect Low-Abundance nuclei Acid Targets, in AnonymousCurrent Protocols in Molecular, Biology, New York, Wiley and Sons, 1995, p 14.8.1

26. Sutkowski N, Kuo M L, Varela-Echavarria A, Dougherty J P, Ron Y: A murine model for B-lymphocyte somatic cell gene therapy. Proceedings of the National Academy of Sciences of the United States of America 91:8875, 1994

27. Gu J, Kuo M L, Rivera A, Sutkowski N, Ron Y, Dougherty J P: A murine model for genetic manipulation of the T cell compartment. Experimental Hematology 24:1432, 1996

28. Goff S, Traktman P, Baltimore D: Isolation and properties of Moloney murine leukemia virus mutants: use of a rapid assay for release of virion reverse transcriptase. Journal of Virology 38: 239, 1981

29. Mulligan R C: The basic science of gene therapy. Science 260:926, 1993

30. Aronow B J, Silbiger R N, Dusing M R, Stock J L, Yager K L, Potter S S, Hutton J J, Wiginton D A: Functional analysis of the human adenosine deaminase gene thymic regulatory region and its ability to generate position-independent transgene expression. Mol Cell Biol 12:4170, 1992

31. Keller G, Snodgrass R: Life span of multipotential hematopoietic stem cells in vivo. J Exp Med 171:1407, 1990

32. Jordan C T, Lemischka I R: Clonal and systemic analysis of long-term hematopoiesis in the mouse. Genes Dev 4:220, 1990

33. Crystal R G: Transfer of genes to humans: early lessons and obstacles to success. Science 270:404, 1995

While certain of the preferred embodiments of the present invention have been described and specifically exemplified above, it is not intended that the invention be limited to such embodiments. Various modifications may be made thereto without departing from the scope and spirit of the present invention, as set forth in the following claims.

We claim:

1. A method for expressing exogenous nucleic acids in myeloid-committed stem cells comprising:
   a) obtaining myeloid-committed stem cells from spleen; and
   b) contacting said cells with a retroviral vector containing at least one nucleic acid encoding a myeloid specific protein, under conditions whereby said vector enters cells and expresses a protein encoded by said at least one nucleic acid.

2. A method as claimed in claim 1, wherein said at least one nucleic acid encoding a myeloid specific protein is operably linked to a myeloid cell specific promoter.

* * * * *

SEQUENCE LISTING

<160> NUMBER OF SEQ ID NOS: 2

<210> SEQ ID NO 1
<211> LENGTH: 17
<212> TYPE: DNA
<213> ORGANISM: Artificial Sequence
<220> FEATURE:
<223> OTHER INFORMATION: Primers

<400> SEQUENCE: 1
caggatgatc tggacga                        17

<210> SEQ ID NO 2
<211> LENGTH: 20
<212> TYPE: DNA
<213> ORGANISM: Artificial Sequence
<220> FEATURE:
<223> OTHER INFORMATION: Primers

<400> SEQUENCE: 2
acgtttaggc agccgtaggt                     20